(12) United States Patent
Rasmussen et al.

(10) Patent No.: US 11,076,999 B2
(45) Date of Patent: Aug. 3, 2021

(54) ABSORBENT ARTICLES AND METHODS OF MAKING

(71) Applicant: 3M INNOVATIVE PROPERTIES COMPANY, St. Paul, MN (US)

(72) Inventors: Jerald K. Rasmussen, Woodville, WI (US); Mahfuza B. Ali, Mendota Heights, MN (US); Bathsheba E. Chong Conklin, St. Paul, MN (US); Andrew P. Klein, St. Paul, MN (US); Scott E. Langer, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 499 days.

(21) Appl. No.: 15/304,139

(22) PCT Filed: Jun. 19, 2015

(86) PCT No.: PCT/US2015/036696
§ 371 (c)(1),
(2) Date: Oct. 14, 2016

(87) PCT Pub. No.: WO2015/200131
PCT Pub. Date: Dec. 30, 2015

(65) Prior Publication Data
US 2017/0112685 A1 Apr. 27, 2017

Related U.S. Application Data

(60) Provisional application No. 62/017,880, filed on Jun. 27, 2014.

(51) Int. Cl.
A61F 13/15 (2006.01)
A61F 13/53 (2006.01)

(52) U.S. Cl.
CPC ........ *A61F 13/53* (2013.01); *A61F 13/15203* (2013.01); *A61F 13/15577* (2013.01);
(Continued)

(58) Field of Classification Search
CPC ................ A61F 13/53; A61F 13/15203; A61F 2013/15463; A61F 2013/530642
(Continued)

(56) References Cited

U.S. PATENT DOCUMENTS

| 4,076,663 A | 2/1978 | Masuda |
| 4,378,411 A * | 3/1983 | Heilmann ............. G03F 7/0388 427/507 |

(Continued)

FOREIGN PATENT DOCUMENTS

| CN | 1441813 | 9/2003 |
| CN | 1561411 | 1/2005 |

(Continued)

OTHER PUBLICATIONS

Omidian, "Modifying Acrylic-Based Superabsorbent. I. Modification of Crosslinker and Comonomer Nature", Journal of Applied Polymer Science, 1994, vol. 54, pp. 241-249.

(Continued)

*Primary Examiner* — Jacqueline F Stephens
(74) *Attorney, Agent, or Firm* — Julie Lapos-Kuchar

(57) ABSTRACT

Described herein are absorbent articles and methods of making such articles. The articles are made by bonding a copolymer onto a substrate to form a core. The absorbent articles are particularly useful in personal care product, e.g., disposable hygiene products.

20 Claims, 1 Drawing Sheet

(52) U.S. Cl.
CPC ............... *A61F 2013/15463* (2013.01); *A61F 2013/530642* (2013.01)

(58) Field of Classification Search
USPC .................................. 604/367, 368, 374, 375
See application file for complete search history.

(56) References Cited

U.S. PATENT DOCUMENTS

| | | | | |
|---|---|---|---|---|
| 4,798,603 | A | * | 1/1989 | Meyer .................. A61F 13/512 604/378 |
| 5,338,766 | A | | 8/1994 | Phan |
| 5,843,057 | A | * | 12/1998 | McCormack .......... A41D 31/02 604/367 |
| 6,001,894 | A | | 12/1999 | Ottersbach |
| 6,103,785 | A | | 8/2000 | Kajikawa |
| 6,258,997 | B1 | | 7/2001 | Johansson |
| 6,417,425 | B1 | | 7/2002 | Whitmore |
| 6,552,245 | B1 | * | 4/2003 | Roessler ............... A61F 13/496 604/367 |
| 6,863,924 | B2 | | 3/2005 | Ranganathan |
| 6,951,911 | B2 | | 10/2005 | Tagawa et al. |
| 7,052,775 | B2 | | 5/2006 | Dohrn et al. |
| 7,125,603 | B2 | | 10/2006 | David |
| 7,521,587 | B2 | | 4/2009 | Busam |
| 7,858,157 | B2 | | 12/2010 | Busam |
| 9,555,148 | B2 | | 1/2017 | Wattebled |
| 2003/0045847 | A1 | | 3/2003 | Whitmore |
| 2004/0077796 | A1 | | 4/2004 | Daniel |
| 2005/0147824 | A1 | | 7/2005 | Myers |
| 2005/0159720 | A1 | | 7/2005 | Gentilcore |
| 2006/0173431 | A1 | * | 8/2006 | Laumer .................. A61L 15/60 604/372 |
| 2007/0202772 | A1 | | 8/2007 | Ikeuchi |
| 2008/0058747 | A1 | | 3/2008 | Singh Kainth |
| 2008/0234645 | A1 | | 9/2008 | Dodge et al. |
| 2010/0015869 | A1 | | 1/2010 | Hartmann |
| 2011/0033696 | A1 | | 2/2011 | Grubish et al. |
| 2011/0301027 | A1 | | 12/2011 | Bitis |
| 2013/0171737 | A1 | * | 7/2013 | Way et al. ............ C08F 120/06 436/129 |
| 2013/0172490 | A1 | * | 7/2013 | Way ...................... C08F 228/02 525/296 |

FOREIGN PATENT DOCUMENTS

| | | |
|---|---|---|
| CN | 102245218 | 11/2011 |
| EP | 0031628 | 7/1981 |
| GB | 1034296 | 6/1964 |
| JP | 11-511183 | 9/1999 |
| JP | 11-333292 | 12/1999 |
| JP | 2003-521349 | 7/2003 |
| JP | 2004-517728 | 6/2004 |
| JP | 2007-099845 | 4/2007 |
| WO | WO 2000-58546 | 10/2000 |
| WO | WO 2008/114847 | 9/2008 |
| WO | WO 2010-015560 | 2/2010 |
| WO | WO 2010/071584 | 6/2010 |
| WO | WO 2013-072268 | 5/2013 |
| WO | WO 2015-200157 | 12/2015 |

OTHER PUBLICATIONS

Pytlik, "Superabsorbent Polymers", [on line], [retrieved from the internet on Nov. 23, 2016], URL <http://wwwcourses.sens.buffalo.edu/ce435/Diapers/Diapers.html>, pp. 8.
Wente, "Superfine Thermoplastic Fibers", Industrial and Engineering Chemistry, Aug. 1956, vol. 48, No. 8, pp. 1342-1346.
Wente, "Manufacture of Superfine Organic Fibers", Naval Research Laboratories Report No. 4364, May 25, 1954, 22 pages.
International Search Report for PCT International Application No. PCT/US2015/036696 dated Oct. 5, 2015, 3 pages.

\* cited by examiner

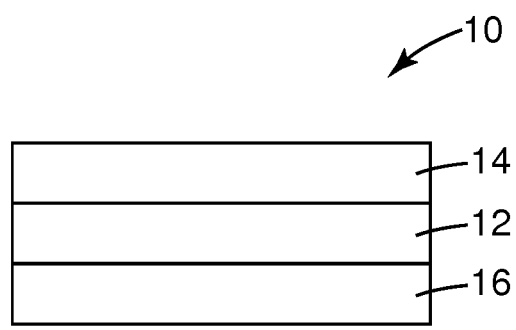

ABSORBENT ARTICLES AND METHODS OF MAKING

CROSS REFERENCE TO RELATED APPLICATIONS

This application is a national stage filing under 35 U.S.C. 371 of PCT/US2015/036696, filed Jun. 19, 2015, which claims the benefit of U.S. Application No. 62/017,880, filed Jun. 27, 2014, the disclosure of which is incorporated by reference in its/their entirety herein.

TECHNICAL FIELD

An absorbent article is described comprising bonded copolymer onto a substrate to form a core and methods of making such articles, which are useful in personal care products.

BACKGROUND

Personal care products for the absorption of body fluids are known. Such products include adult incontinence products, diapers, training pants, feminine care products, wound dressings and the like. Traditionally, such personal care products generally comprise an amount of a cellulosic fiber such as wood pulp fluff. Wood pulp fluff is known to be a suitable absorbent for body fluids. As a general rule, 1 gram of wood pulp fluff is able to absorb from about 5 to about 8 grams of a discharged body fluid such as urine. A personal care product such as an infant diaper, generally has an absorbent capacity of at least about 200 to 400 grams of urine. Thus, when such an infant diaper is formed from wood pulp fluff, a relatively large quantity of wood pulp fluff must be employed.

In order to reduce the amount of wood pulp fluff and the corresponding bulk of such an infant diaper, it is known to include high absorbency materials known in the art as superabsorbents. Such high absorbency materials are generally capable of absorbing at least about 10, preferably at least about 20, and up to 50 or more times their weight in water. By incorporating such high absorbency materials in infant diapers, it is possible to reduce the overall bulk of the diaper while maintaining its absolute absorbent capacity.

Nonetheless, the use of such high absorbency materials is not without problems. For example, some high absorbency materials are known to cause gel blocking. That is, as the high absorbency materials become swollen with a liquid, they form a gelatinous mass which prevents the free flow of liquid therethrough. Thus, while the high absorbency materials may be able to absorb an initial insult (in other words, exposure to fluid), subsequent insults are unable to pass through the now swollen high absorbency material. As a result, subsequent insults tend to pool and run off of the absorbent product resulting in leakage.

SUMMARY

There is a desire for absorbent articles, which have high absorbency capacity and a rapid absorption rate. There is a desire to provide thin absorbent articles with a high absorbent capacity. There is also a desire to be able to easily control or tailor the absorbency capacity of absorbent articles to the desired end use application without compromising the rapid absorption rate. There is a need to provide facile processes that are amenable to roll-to-roll processing, and thus provide ease of manufacturing.

In one aspect, an absorbent article is described comprising: (i) a first substrate; and (ii) a copolymer irreversibly bonded onto the first substrate to form a core, wherein the copolymer is derived from: (i) a first monomer selected from a (meth)acrylic acid or salt thereof; (ii) a second monomer, wherein the second monomer is hydrophilic; and (iii) greater than 1 wt % of a third monomer, wherein the third monomer is a hydrophilic crosslinking monomer, wherein at least 50% of the acidic functional groups in the core are neutralized with salt forming cations.

In another aspect, a method of making an absorbent article is described comprising: (a) contacting a polymerizable solution to a first substrate, wherein the polymerizable solution comprises (i) a first monomer selected from a (meth)acrylic acid or salt thereof; (ii) a second monomer, wherein the second monomer is hydrophilic; and (iii) greater than 1 wt % of a third monomer, wherein the third monomer is a hydrophilic crosslinking monomer; and (b) polymerizing the polymerizable solution to irreversibly bond a copolymer onto the first substrate forming a core, wherein at least 50% of the acidic functional groups in the core are neutralized with salt forming cations.

The above summary is not intended to describe each embodiment. The details of one or more embodiments of the invention are also set forth in the description below. Other features, objects, and advantages will be apparent from the description and from the claims.

BRIEF DESCRIPTION OF DRAWINGS

In the accompanying drawing:
FIG. 1 is a schematic of an absorbent article, 10, of the present disclosure.

DETAILED DESCRIPTION

As used herein, the term
"a", "an", and "the" are used interchangeably and mean one or more;

"and/or" is used to indicate one or both stated cases may occur, for example A and/or B includes, (A and B) and (A or B); and "(meth)acrylate" refers to compounds containing either an acrylate ($CH_2$=$CHCO^-$) or a methacrylate ($CH_2$=$CCH_3CO^-$) structure or combinations thereof.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

The present disclosure is directed toward an absorbent core. Such cores can be used in personal care products. In the present disclosure, the core comprises a substrate that has a copolymer bonded thereon.

Substrate

The substrate is not particularly limited so long as a copolymer is bonded thereon. The substrate may be a particle, fiber, film, or sheet. The substrate may be a woven or a nonwoven. The substrate may be from a natural fiber, such as cotton, or a synthetic fiber such as a thermoplastic polymer.

Suitable particles include, but are not limited to, organic particles (such as carbon, activated carbon, styrene divinyl benene, crosslinked (meth)acrylates, organically modified inorganic particles, etc.), and inorganic particles (such as glass, ceramics, or metal oxides including silica, alumia, etc.). The particles may be porous or nonporous particles. Typically the particles have an average diameter of at least 0.1, 1, 5, 10, 20, or even 40 micrometers (μm) to at most 75 μm, 100 μm, 500 μm, 1 millimeter (mm), 2 mm, 4 mm, 6.5 mm, or even 7 mm, although other size ranges may be contemplated based on the application. The particles could be used as an individual particle or the particles could be incorporated into another substrate for use, such as a nonwoven web.

The substrate may be a film or sheet. In one embodiment the thickness of the fiber, film or sheet is no more than 5 mm (millimeter), 2 mm, 1 mm, 500 μm (micrometer), 100 μm, 20 μm, 2 μm, or even 1 μm.

In a preferred embodiment, the substrate is a nonwoven web which may include nonwoven webs manufactured by any of the commonly known processes for producing nonwoven webs. As used herein, the term "nonwoven web" refers to a fabric having a structure of individual fibers or fibers that are interlaid, but not in an identifiable manner as in a knitted or woven fabric.

Nonwoven webs can be made by wet laid, carded, air laid, spunlaced, spunbonding or melt-blowing techniques or combinations thereof. Spunbonded fibers are typically small diameter fibers that are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to from a web of randomly dispersed meltblown fibers. Any of the non-woven webs may be made from a single type of fiber or two or more fibers that differ in the type of thermoplastic polymer and/or thickness.

Further details on the manufacturing method of nonwoven webs of this disclosure may be found in Wente, Superfine Thermoplastic Fibers, 48 INDUS. ENG. CHEM. 1342 (1956), or in Wente et al., Manufacture Of Superfine Organic Fibers, (Naval Research Laboratories Report No. 4364, 1954).

Suitable thermoplastic polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), polyesters such as poly(lactic acid), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

Suitable polyolefins include, but are not limited to, poly(ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, typical nylon polymers such as poly(iminoadipoyliminohexamethylene), poly(iminoadipoyliminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

In some embodiments, the thermoplastic polymer substrate may be surface treated, such as by corona or plasma discharge, to provide suitable functionality to the surface of the substrate. Surface treatment can provide functional groups such as hydroxyl groups that can improve wetting by the polymerizable solution or that can improve the degree of grafting of the copolymer. One such useful plasma treatment is described in U.S. Pat. No. 7,125,603 (David et al.).

In one embodiment, the substrate is a porous substrate, for example a microporous membrane such as a solvent-induced phase separation (SIPS) membrane or a thermally-induced phase separation (TIPS) membrane, which are known in the art.

Copolymer

The substrate is surface modified with a copolymer, which is bonded upon the substrate. The copolymer may be grafted to the substrate and/or crosslinked onto the substrate, forming a polymer network that is not easily removed from the substrate. The copolymer is derived from at least three different monomers: (i) a (meth)acrylic acid monomer or salt thereof; (ii) a non-crosslinking hydrophilic monomer; and (iii) a cross-linking hydrophilic monomer.

The (meth)acrylic acid monomer includes acrylic acid and salts thereof and/or methacrylic acid and salts thereof. Suitable salts of (meth)acrylic acid include those known in the art, including alkali metal salts, ammonium salts, amine salts, etc.

The second monomer is a non-crosslinking hydrophilic monomer. These monomers can be selected to assist in increasing the absorption amount and/or improving the absorption time of the absorbent core. Suitable second monomers include monoethylenically unsaturated compounds (or compounds having a polymerizable double bond) having at least one hydrophilic radical, such as carboxyl, carboxylic acid anhydride, carboxylic acid salt, sulfonic acid, sulfonic acid salt, hydroxyl, ether, amide, amino, and quaternary ammonium salt groups. The second monomer does not include a (meth)acrylic acid monomer or salt thereof. Examples of suitable second monomer include the following.

Carboxyl group-containing monomers including monoethylenically unsaturated mono or poly-carboxylic acids such as, maleic acid, fumaric acid, crotonic acid, sorbic acid, itaconic acid, and cinnamic acid.

Carboxylic acid anhydride group-containing monomers including monoethylenically unsaturated polycarboxylic acid anhydrides (such as maleic anhydride).

Carboxylic acid salt-containing monomers including water-soluble salts (alkali metal salts, ammonium salts, amine salts, etc.) of monoethylenically unsaturated mono- or poly-carboxylic acids [such as sodium maleate, methylamine maleate, sodium fumarate, and potassium itaconate].

Sulfonic acid group-containing monomers including aliphatic or aromatic vinyl sulfonic acids (such as vinylsulfonic acid, allyl sulfonic acid, vinyltoluenesulfonic acid, styrene sulfonic acid), and (meth)acrylic sulfonic acids [such as sulfopropyl (meth)acrylate, 2-hydroxy-3-(meth)acryloxy propyl sulfonic acid].

Sulfonic acid salt group-containing monomers including alkali metal salts, ammonium salts, and amine salts of sulfonic acid group-containing monomers as mentioned above.

Hydroxyl group-containing monomers including monoethylenically unsaturated alcohols [such as (meth)allyl alcohol], monoethylenically unsaturated ethers or esters of polyols (alkylene glycols, glycerol, polyoxyalkylene polyols), such as hydroxethyl (meth)acrylate, hydroxypropyl (meth) acrylate, triethylene glycol (meth)acrylate, and poly(oxyethylene oxypropylene) glycol mono (meth)allyl ether (in which hydroxyl groups may be etherified or esterified).

Amide group-containing monomers including vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N'-di-n-propylacrylamide), N-hydroxyalkyl (meth) acrylamides [such as N-methylol(meth)acrylamide, N-hydroxyethyl (meth)acrylamide], N,N-dihydroxyalkyl (meth)acrylamides [such as N,N-dihydroxyethyl (meth) acrylamide], and vinyl lactams (such as N-vinylpyrrolidone).

Amino group-containing monomers including amino group-containing esters (e.g. dialkylaminoalkyl esters, dihydroxyalkylaminoalkyl esters, morpholinoalkyl esters, etc.) of monoethylenically unsaturated mono- or di-carboxylic acid [such as dimethlaminoethyl (meth)acrylate, diethylaminoethyl (meth)acrylate, morpholinoethyl (meth)acrylate, dimethyl aminoethyl fumarate], and heterocyclic vinyl compounds [such as vinyl pyridines (e.g. 2-vinyl pyridine, 4-vinyl pyridine, N-vinyl pyridine), N-vinyl imidazole].

Quaternary ammonium salt group-containing monomers including N,N,N-trialkyl-N-(meth)acryloyloxyalkylammonium salts [such as N,N,N-trimethyl-N-(meth)acryloyloxyethylammonium chloride, N,N,N-triethyl-N-(meth)acryloyloxyethylammonium chloride, 2-hydroxy-3-(meth) acryloyloxypropyl trimethyl ammonium chloride], and monomers as mentioned in British patent specification No. 1,034,296.

These second monomers have a polymerizable double bond and are water-soluble or become water-soluble by hydrolysis. Water-soluble monomers which do not need hydrolysis after polymerization are preferred from the viewpoint of providing an easy process for producing water-absorbing resins. Further, from the viewpoint of providing water-absorbing resins having a high water-absorbence, the preferred water-soluble monomers are carboxyl group-containing monomers such as (meth)-acrylic acid and maleic acid anhydride; carboxylic acid salt group-containing monomers such as sodium (meth)acrylate, trimethylamine (meth) acrylate and triethanolamine (meth)acrylate, and quaternary ammonium salt group-containing monomers such as N,N, N-trimethyl-N-(meth)acryloyloxyethylammonium chloride. Most preferred superabsorbent forming second monomers in the present disclosure include, for example, maleic acid, fumaric acid, crotonic acid, sorbic acid, itaconic acid, cinnamic acid, vinyl sulfonic acid, allyl sulfonic acid, vinyl toluene sulfonic acid, styrene sulfonic acid, sulfo(meth) acrylate, sulfopropyl(meth)acrylate, 2-acrylamide-2-methylpropane sulfonic acid, 2-hydroxyethyl(meth)acryloylphosphate, phenyl-2-acryloyloxyethylphosphate, the sodium, potassium and ammonium salts thereof, maleic anhydride and combinations thereof.

Preferred second monomers used in this disclosure include those selected from at least one of 2-hydroxyethylmethacrylate, 2-hydroxypropyl(meth)acrylate, 3-hydroxypropyl(meth)acrylate, N,N-dimethylacrylamide, acrylamide, and combinations thereof.

Surprisingly, it has been discovered in the present disclosure that by using greater than 1% by weight of a second monomer, adequate absorbance results can be achieved for the core. In one embodiment, at least 1%, 2%, 3%, 4%, or even 5% by weight and no more than 30%, 25%, or even 20% by weight of the second monomer versus the total weight of monomer should be used.

The copolymer of the present disclosure, further comprises a third monomer, which is a hydrophilic crosslinking monomer.

Suitable crosslinking monomers are those compounds having two or more ethylenically unsaturated groups capable of copolymerizing with the first and the second monomers.

Exemplary third monomers include: N,N'-methylene bisacrylamide, N,N'-methylene bismethacrylamide, bis(2-methacryloxyethyl) phosphate, 1,4-butanediol diacrylate, 1,4-butanediol dimethacrylate, diethylene glycol diacrylate, diethylene glycol dimethacrylate, glycerol trimethacrylate, triallyl cyanurate, triethylene glycol diacrylate, or others such as known in the art in order to produce a cross-linked and/or branched graft polymer and the like. Preferred third monomers include those selected from at least one of methylenebisacrylamide, polyethyleneglycoldiacrylate, and combinations thereof.

Previously, it has been thought that the amount of crosslinker used in absorbent articles needed to be kept low to provide sufficient absorbance capacity. See for example Omidian, H., et al. in *Journal of Applied Polymer Science*, vol. 54, (1994), p. 241-249, with is directed toward acrylic-based superabsorbents and teaches that the absorption is dependent on the amount of crosslinker used, indicating that the amount of crosslinker needs to be kept low. Also see U.S. Pat. No. 6,417,425 (Whitmore et al.) which discloses an absorbent article made via a grafting process using less than about 1 mole percent of crosslinker.

Surprisingly, in the present disclosure, it has been found that using at least 1 wt % of the crosslinking monomer versus the total monomer weight results in good absorption properties. The amount of third monomer (the crosslinking monomer) employed in the present disclosure will depend on the nature of the third monomer and the polymerization method used. If too little crosslinking occurs, the copolymer can be rinsed from the surface of the substrate. This is particularly relevant when using a Type I photoinitiator, as opposed to a Type II photoinitiator, since covalent grafting of the polymerizable solution to the surface does not occur. If too much crosslinking occurs, absorbency capacity decreases, or the rate of absorption decreases, or both. In one embodiment, at least 1%, 2%, 3%, 4%, or even 5% by weight and no more than 30%, 25%, 20%, 15%, or even 10% by weight of the third monomer versus the total weight of monomer can be used.

The copolymer described here is a polymer comprising repeating units derived from the recited monomers described above. Additional monomers may be copolymerized with the monomers described above to yield a copolymer with specific properties.

In one embodiment, the copolymer is derived from just three different monomers, one first monomer, one second monomer, and one third monomer. In another embodiment, the copolymer is derived from more than three different monomers, including for example one or more different first monomers, one or more different second monomers, and one or more different third monomers. In yet another embodiment, the copolymer is derived from more than three different monomers, including for example one or more different first monomers, one or more different second monomers, one or more different third monomers, and one or more different fourth monomers, wherein the fourth monomer is not hydrophilic and less than about 10%, 8%, 5%, 4%, 2%, or even 1% by weight of the fourth monomer is used.

Method of Making

The copolymer of the present disclosure is irreversibly bonded upon the substrate. As used herein irreversibly bonded means that the copolymer is either covalently bonded to the substrate and/or is physically crosslinked onto the substrate such that, when the composite containing the polymerized copolymer is soaked in deionized water for at least 30 minutes, the copolymer remains firmly attached to the substrate. That is, the copolymer does not dissolve or wash away, and the physical presence of the swollen copolymer on the surface of the substrate is obvious by visual or tactile observation. In the present disclosure, a polymerizable solution is prepared comprising the monomers, a solvent, and, optionally, a photoinitiator.

In one embodiment, a polymeric porogen is added to the polymerizable solution to create permanent pores in the polymerized copolymer as disclosed in U.S. patent Ser. No. 10/039,856 (Rasmussen et al.), herein incorporated by reference in its entirety. Exemplary polymeric porogens include: polyethylene glycol, polypropylene glycol, and combinations thereof.

In the method of the present disclosure, the photoinitiator may be Type I or Type II.

When using Type I initiators, the copolymer is physically crosslinked onto the substrate. Type I initiators work via an alpha-cleavage which forms two radical species. At least one of the radical species initiates polymerization of the monomer(s). Incorporation of the crosslinking monomer(s) results in a crosslinked coating on the surface of the substrate. Exemplary Type I initiators include benzoin ethers such as benzoin methyl ether and benzoin isopropyl ether; substituted acetophenones such as 2,2-dimethoxyacetophenone, available under the trade designation "IRGACURE™ 651" photoinitiator (Ciba Specialty Chemicals), 2,2 dimethoxy-2-phenyl-1-phenylethanone, available under the trade designation "ESACURE KB-1" photoinitiator (Sartomer Co.; West Chester, Pa.), 1-[4-(2-hydroxyethoxy)phenyl]-2-hydroxy-2-methyl-1-propan-1-one, available under the trade designation "IRGACURE 2959" (Ciba Specialty Chemicals), and dimethoxyhydroxyacetophenone; substituted α-ketols such as 2-methyl-2-hydroxy propiophenone; aromatic sulfonyl chlorides such as 2-naphthalene-sulfonyl chloride; and photoactive oximes such as 1-phenyl-1,2-propanedione-2-(O-ethoxy-carbonyl)oxime. Particularly preferred among these are the substituted acetophenones, and especially 1-[4-(2-hydroxyethoxy)phenyl]-2-hydroxy-2-methyl-1-propan-1-one due to its water solubility.

Type II initiators work to facilitate hydrogen abstraction from the surface of the substrate to provide an incipient free radical, and free radical addition of the monomer(s) to produce the grafted copolymer. When using Type II initiators, the copolymer is typically grafted onto the substrate, however the copolymer may be physically crosslinked onto the substrate as well. In order for the grafting of the copolymer to occur, the substrate must comprise an abstractable atom (e.g., a hydrogen or halogen). Type II initiators used in the present disclosure include those of the general formula:

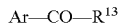

$$Ar-CO-R^{13}$$

in which Ar is a substituted or unsubstituted aryl group having 6 to 12 carbon atoms optionally substituted with a $C_1$ to $C_{12}$ alkyl group, a $C_1$ to $C_{12}$ alkoxy group, or a phenyl group; and $R^{13}$ is a $C_1$ to $C_6$ alkyl group, a cycloalkyl group having 3 to 14 carbon atoms, or Ar. Exemplary Type II initiators include benzophenone, 4-(3-sulfopropyloxy)benzophenone sodium salt, Michler's ketone, benzil, anthraquinone, 5,12-naphthacenequinone, aceanthracenequinone, benz(A)anthracene-7,12-dione, 1,4-chrysenequinone, 6,13-pentacenequinone, 5,7,12,14-pentacenetetrone, 9-fluorenone, anthrone, xanthone, thioxanthone, 2-(3-sulfopropyloxy)thioxanthen-9-one, acridone, dibenzosuberone, acetophenone, and chromone.

An effective amount of Type I or Type II initiator is used to trigger polymerization of the monomer and enable grafting or coating of the copolymer onto the substrate. The photoinitiators can be used in amounts from about 0.001 part by weight to about 15 parts, preferably from about 0.5 to about 5 parts, by weight based on 100 parts total monomer.

A solvent may be used in the polymerizable solution to solubilize the monomers and the optional photoinitiator. The solvent may be any polar solvent. In many embodiments the solvent is water or a water/water-miscible organic solvent mixture. The ratio of water to organic solvent can vary widely, but is typically greater than about 1:2 (v/v) water to organic solvent. Water is an important component of the solvent mixture for solubility purposes, especially when a portion of the first monomer component is in its neutralized form. The organic solvent may be an important component of the solvent mixture for the purpose of improving the wetting of the substrate, especially when the substrate is hydrophobic. The organic solvent can also promote solubility of the photoinitiator in the mixture.

Any such water miscible organic solvent preferably has no groups that would retard the polymerization. In some embodiments, the water miscible solvents are protic containing organic liquids such as the lower alcohols having 1 to 4 carbon atoms, lower glycols having 2 to 6 carbon atoms, and lower glycol ethers having 3 to 6 carbon atoms and 1 to 2 ether linkages. Specific examples are methanol, ethanol, isopropanol, n-butanol, t-butyl alcohol, ethylene glycol, methoxyethanol, ethoxyethanol, propoxyethanol, butoxyethanol, methyl carbitol, ethyl carbitol, and mixtures thereof.

In other embodiments, non-protic water miscible organic solvents can also be used such as ketones, amides, and sulfoxides such as acetone, methyl ethyl ketone, methyl propyl ketone, dimethylformamide, dimethylacetamide, and dimethyl sulfoxide.

The concentration of each component in the polymerizable solution may vary depending on a number of factors including, but not limited to, the identity of the monomers in the polymerizable solution, the identity of the initiator, the extent of grafting or crosslinking desired, the reactivity of the monomer(s), and the solvent used.

Typically, the total solids in the polymerizable solution ranges from about 0.1 wt % to about 60 wt %, desirably, from about 1 wt % to about 35 wt %, more desirably, from about 5% to about 25%, based on a total weight of the polymerizable solution.

In the present disclosure, the substrate is contacted with the polymerizable solution (comprising at least the monomers, the solvent, and the optional photoinitiator) to form a treated substrate. The substrate may be imbibed or coated with the polymerizable solution using conventional techniques known in the art, including but not limited to, dip coating, roll coating, spray coating, knife coating, gravure coating, extrusion, die-coating, and the like.

After the substrate has been treated with the polymerizable solution it is often desirable to remove the excess treatment fluid by squeezing and/or blotting, and this is particularly desirable when it is desired to form a thin coating of bonded polymer on the surface of a nonwoven web or film or foam material. This may be done by the simple expedient of passing the treated substrate through a nip formed between rollers, such as rubber or rubber coated rollers, to squeeze off the excess treatment fluid, and/or vacuum suction, and/or by blotting the treated substrate with absorbent media such as paper or cloth towels or the like.

However, it may also be highly desirable for certain applications that one or both surfaces of a substrate such as a polymeric film material be covalently bonded or coated with a thicker coating of the copolymer such that the bonded copolymer may serve as a coating of hydrogel. Such hydrogel coated films are useful for many medical applications including, but not limited to, such as defibrillator pads, cardiac monitoring electrode pads, transdermal drug delivery patches, and the like. Where a thicker coating of the bonded copolymer is desired it may be desirable to avoid removing excess treatment fluid.

The treated substrate, coated with the polymerizable solution, then is subjected to an activation energy to polymerize or graft the monomers onto the substrate. The activation energy generates free radicals in solution (by cleaving at least some of the Type I photoinitiator molecules to form free radicals) or on the surface of the substrate (by exciting the Type II photoinitiator molecules which then abstract an atom from the substrate). Electron beam or gamma irradiation can also be used to provide the activation energy necessary to generate free radicals in solution or on the surface of the substrate (the addition of a photoinitiator is not necessary in these cases). The free radicals then initiate polymerization of the monomer either in solution or starting at the surface radical sites which were formed by exposure to the activation energy.

The activation energy may be provided by methods as are known in the art, such as for example by exposure to ultraviolet radiation, electron beam radiation, or gamma radiation. The conditions under which the irradiation is conducted, such as radiation intensity and time may differ depending on the type of substrate used, the amount of monomer applied to the substrate, the type of irradiation, and the like.

Radiation may be applied using a conventional ultraviolet radiation (UV) such as may be provided by excimer lamp or other UV emitting lamp. Irradiation is generally conducted using a UV lamp with an intensity in the range of from 100 to 700 watts per inch ("W/in"), preferably in the range of from 400 to 600 W/in for 0.1 seconds to 15 minutes or more, with the distance between the UV lamp and the substrate being 2 to 30 centimeters.

Electron beam polymerization or grafting can be accomplished using a commercially available electron beam accelerator, such as those available under the trade designation ELECTOCURTAIN CB 175 (Energy Sciences, Inc., Wilmington, Ma.). Accelerators operating in the 150 to 300 kilovolt range are acceptable. The beam current on such systems, typically 1 to 10 milliamperes, can be adjusted to obtain the desired dose of ionizing radiation. In general, it is desirable to irradiate the coated substrate with doses from about 1 to 16 megarads, more preferably 2 to 8 megarads. Particularly when using lower doses, it is desirable to purge oxygen from the polymerizable solution (as by bubbling nitrogen through the solution). The maximum dose would be that dose at which degradation of the substrate begins.

Desirably, the coated substrate will be subjected to the activation energy in a reduced oxygen or non-oxidative environment, such as by placing the coated substrate in a reaction vessel or passing the polymeric substrate through a reaction chamber from which the air has been purged prior to energy activation of the monomer. The air may be purged from such a reaction vessel or chamber by purging with inert gas such as argon or nitrogen. This is desirable because atmospheric oxygen can act as a reaction terminator by combining with the surface radical sites formed from the radical forming groups on the surface of the substrate, and thereby reduce the number of initialization sites available to the monomer. In many instances it is sufficient to sandwich the coated substrate between two sheets of a thermoplastic polymeric film, such as polyester or polyolefin film.

The temperature during irradiation is not critical and may be done at room temperature.

Although thermal processes are not preferred for reasons of solvent volatility, thermal polymerization or curing of the treated substrate is possible. For thermal curing there are no particular limitations on the type of reaction vessel used. For batch polymerizations, sprayed webs may be cured in an oven in an air or inert atmosphere, and optionally under vacuum. In the case of a continuous process, the web may be passed through a dryer, such as an infrared ("IR"), through air or the like. The polymerization temperature can vary depending on the thickness of the substrate, the concentration of monomer, the type of solvent used, and the type and amount of thermal initiator used in the blend. The polymerization is typically in the range of from 0° C. to 150° C. and preferably in the range of from 10° C. to 100° C., and more preferably in the range of 20° C. to 50° C. The polymerization time depends on the polymerization temperature and the identity of the initiator, but is typically several seconds to 2 hours and preferably several seconds to 10 minutes. Preferred initiators for thermal processes are redox initiators, many of which are well known in the art.

After irradiation, the coated substrate may optionally be washed to remove unpolymerized monomer(s), noncrosslinked polymer, and/or nongrafted polymer, if desired.

After irradiation and optional washing, the substrate with the covalently bonded copolymer thereon may be dried to remove the solvent by such means as forced air ovens, infrared lamps and the like.

The substrate with the copolymer bonded thereon can be processed either in a batch to batch process or a continuous process. In a preferred embodiment, the substrate comprises a sufficient length, such that the substrate (e.g., a web) is processed in a continuous fashion, through for example, coating with the polymerizable solution, irradiation, and optional washing and drying; making a roll good and enabling the high throughput manufacture of an absorbent core.

Depending on the desired end use for the substrate with the copolymer bonded thereon, it may be desirable to convert the acidic monomer or polymer to its conjugate base form before, during, or after processing. While both the acid form of the polymer and the conjugate base form of the polymer are hydrophilic and allow the coated polymeric substrate material to be wetted with aqueous liquids, the conjugate base form is preferred for end uses where high liquid absorbency is desired. The polymer may be converted to its conjugate base form by methods known in the art such as a neutralization reaction with up to a molar equivalent of a strong base such as sodium hydroxide or potassium hydroxide to yield the conjugate base/conjugate acid salt. For example, sodium acrylate or potassium acrylate would result from the neutralization of an acrylic acid monomer using the two bases disclosed above. Where desired, partial neutralization might be accomplished by titrating the acid groups with the base such that less that 100 percent conversion to the salt form is achieved.

The resulting core, comprising the substrate with the copolymer bonded thereon, is neutralized such that no more than 100% and at least 50, 60, 70, 80, 90, or even 95% of the acidic functional groups in the core are neutralized with salt forming cations.

The core, in an absorbent product, is a layer or particle used to contain the bulk of the liquid assault. Therefore, the core should have a rapid uptake of the liquid and minimal gel blocking. Ideally, it is preferable if the core can absorb at least 10 times, 20 times, 40 times or even 50 times its weight in deionized water and at least 5 times, 10 times, 15 times, or even 20 times its weight in urine. Depending on the application, in one embodiment, it may be preferable that the core absorb liquid in a quick fashion, for example absorbing liquid (such as deionized water or saline) in less than 90 sec, 60 sec, 40 sec, 20 sec, or even 10 sec when tested using the Test method of liquid absorption rate given in the Example section.

The absorbent structures or cores, described above are suitable for use in disposable absorbent products such as diapers, training pants, adult incontinence products, feminine care products, animal care products, wound dressings, chemical absorbent pads, and the like. Methods of forming such absorbent products and the absorbent products formed thereby are known to those skilled in the art.

The core described above, may be used alone or may be combined with one or more layers to form an absorbent article as shown in FIG. 1. Core 12 comprises a first substrate with a copolymer covalently bonded thereon. Core 12 may be contacted with second substrate 14, which is a liquid pervious layer. Optionally, or in addition to second substrate 14, core 12 may be contacted with third substrate 16, which is a liquid impervious layer. If both second substrate 14 and third substrate 16 are present, core 12 is sandwiched therebetween. The second substrate 14 and third substrate 16 may be directly contacting core 12, or there may be optional layers therebetween to facilitate construction or performance, for example adhesive layers between the substrates or an additional layer(s) to provide enhanced properties such as performance. However, second substrate 14 is in liquid communication with core 12. Optionally, third substrate 16 is in liquid communication with core 12.

Typically an absorbent product comprises a liquid pervious layer, or second substrate, between the body of the subject and the core. This liquid pervious layer should exhibit rapid uptake of fluid, good transfer properties, good uptake upon repeated insults with fluid, and good skin compatibility, among other things. Such liquid pervious layers are known in the art and can include, for example, porous polyesters, porous polyolefins, porous rayon, cotton, and combinations thereof.

Typically an absorbent product comprises a liquid impervious layer, or third substrate, which contains the liquid within the absorbent product, preventing leakage or seepage of the fluid. Such liquid impervious layers are known in the art and can include, for example, a nonporous polyolefin.

The following is a list of exemplary embodiments of the present disclosure:

Embodiment 1

An absorbent article comprising:
a first substrate; and
a copolymer irreversibly bonded onto the first substrate to form a core,
  wherein the copolymer is derived from:
    a first monomer selected from a (meth)acrylic acid or salt thereof;
    a second monomer, wherein the second monomer is hydrophilic; and
    greater than 1 wt % of a third monomer, wherein the third monomer is a hydrophilic crosslinking monomer,
wherein at least 50% of the acidic functional groups in the core are neutralized with salt forming cations.

Embodiment 2

The absorbent article of embodiment 1, wherein the second monomer is selected from at least one of 2-hydroxyethylmethacrylate, 2-hydroxypropyl(meth)acrylate, 3-hydroxypropyl(meth)acrylate, N,N-dimethylacrylamide, and acrylamide.

Embodiment 3

The absorbent article of any one of the previous embodiments, wherein the copolymer comprises at least 1% of the second monomer.

Embodiment 4

The absorbent article of any one of the previous embodiments, wherein the third monomer is selected from at least one of methylenebisacrylamide and polyethyleneglycoldiacrylate.

Embodiment 5

The absorbent article of any one of the previous embodiments, further comprising a second layer, wherein the second layer is a liquid pervious layer.

Embodiment 6

The absorbent article of embodiment 5, wherein the second layer is selected from polyester, polyolefin, rayon, cotton, and combinations thereof.

Embodiment 7

The absorbent article of any one of embodiments 5 or 6 further comprising a third layer, wherein the third layer is a liquid impervious layer and the core sandwiched between the second layer and the third layer.

Embodiment 8

The absorbent article of embodiment 7, wherein the third layer is selected from a polyolefin.

Embodiment 9

The absorbent article of any one of the previous embodiments, wherein the first substrate is selected from at least one of a thermoplastic and a fabric.

Embodiment 10

The absorbent article of any one of the previous embodiments, wherein the first substrate is selected from at least one of a polypropylene, polyethylene, Nylon X, cotton, and cellulose.

Embodiment 11

The absorbent article of any one of the previous embodiments, wherein the absorbent article is selected from a diaper, a feminine hygiene pad, an animal hygiene pad, a wound care article, and a chemical absorbent pad.

Embodiment 12

A method of making an absorbance article comprising:
(a) contacting a polymerizable solution to a first substrate, wherein the polymerizable solution comprises (i) a first monomer selected from a (meth)acrylic acid or salt thereof; (ii) a second monomer, wherein the second monomer is hydrophilic; and (iii) greater than 1 wt % of a third monomer, wherein the third monomer is a hydrophilic crosslinking monomer; and
(b) polymerizing the polymerizable solution to irreversibly bond a copolymer onto the first substrate forming a core,
wherein at least 50% of the acidic functional groups in the core are neutralized with salt forming cations.

Embodiment 13

The method of embodiment 12, wherein the polymerizable solution further comprises a photoinitiator.

Embodiment 14

The method of embodiment 13, wherein the photoinitiator is a Type II.

Embodiment 15

The method of any one of embodiments 12-14, wherein the polymerizable solution is contacted to the first substrate by a coating process.

Embodiment 16

The method of embodiment 15, wherein the coating process comprises at least one of: knife coating, gravure coating, and dip coating.

Embodiment 17

The method of any one of embodiments 12-16, wherein the polymerization is initiated with UV or e-beam radiation.

Embodiment 18

The method of any one of embodiments 12-17, further comprising washing the core.

Embodiment 19

The method of any one of embodiments 12-18, further comprising drying the core.

Embodiment 20

The method of any one of embodiments 12-19, where the absorbent article is a roll good.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: g=gram, gsm=grams of polymer per square meter, kg=kilograms, sec=seconds, min=minutes, mol=mole; cm=centimeter, mm=millimeter, mL=milliliter, L=liter, v=volume, and wt=weight.

Test Methods

Test Method for Liquid Absorption Amount

Three 24 mm diameter disks were die-cut from each sample, individually weighed, then placed into 5 mL polypropylene centrifuge tubes containing 4.5 mL of liquid (deionized water or 0.9% wt/wt saline (sodium chloride solution)). The centrifuge tubes were capped and gently rotated for 15 min. The swollen disks were removed with forceps, allowed to drip for 60 sec to remove excess liquid, and then reweighed. The absorption amount, $A_x$, expressed in grams of liquid absorbed per gram of composite substrate (g/g), was calculated according to the following equation:

$$A_x=(W_w-W_d)/W_d$$

where $W_w$ is the wet weight of the disk and $W_d$ is the dry weight of the disk. Results are recorded as the average of the three measurements.

Test Method for Liquid Absorption Rate

A qualitative test was devised to compare the absorption rates of various samples. Two drops of liquid (deionized water or 0.9% wt/wt saline) were deposited from a polypropylene disposable pipet onto the substrate. The length of time needed for the liquid to be completely absorbed into the material was observed, and recorded as the absorption time $(A_t)$ in sec. Each sample was tested in triplicate and the average was reported.

Preparation of S-BP:
4-(3-sulfopropyloxy)benzophenone, Sodium Salt

Sodium hydride (6 grams of a 60% by weight dispersion in mineral oil) was weighed into a 500 mL round bottom flask. Petroleum ether (15 mL) was added and swirled to dissolve the mineral oil. The liquid was decanted. Washing was repeated two more times with petroleum ether, decanting each time. Tetrahydrofuran (200 mL) was then added to the flask. Solid 4-hydroxybenzophenone (19.8 grams) was added portion-wise over a period of about 10 min to control the rate of gas evolution. The resultant yellow mixture was stirred for 30 min, propane sultone (13.4 grams, Alfa Aesar, Ward Hill, Mass.) was added, stirred for 30 min, then refluxed overnight. The mixture was cooled to room temperature, isopropanol (15 mL) was added, stirred 30 min, and the solid was filtered, and dried under a stream of nitrogen to provide the desired product (33.8 grams) as an off-white solid. A 0.1 gram/mL solution in deionized water was prepared for use with the example preparations below.

Preparation of Monomer Stock Solution

A monomer solution (20% wt/wt acrylic acid, 75% neutralized with sodium hydroxide) was prepared from acrylic acid (12.27 grams), 5 N sodium hydroxide solution (25.56 mL), diluted to a total of 60 grams with a 1:1 v/v mixture of ethanol and deionized water.

Comparative Example C1

20% solids solution: A polymerizable solution was prepared by mixing about 5.0 g of Monomer Stock Solution with 250 μL of S-BP. Various amounts of methylenebisacrylamide (MBA) was added to the polymerizable solution to provide varying amounts of crosslinker based on total monomer weight.

15% solids solution: A polymerizable solution was prepared by diluting about 3.6 g of Monomer Stock Solution with 1:1 v/v mixture of ethanol and deionized water to achieve about 5.0 g and adding 250 μL of S-BP. Various amounts of methylenebisacrylamide (MBA) was added to the polymerizable solution to provide varying amounts of crosslinker based on total monomer weight.

10% solids solution: A polymerizable solution was prepared by diluting about 2.5 g of Monomer Stock Solution with 1:1 v/v mixture of ethanol and deionized water to achieve about 5.0 g and adding 250 μL of S-BP. Various amounts of MBA was added to the polymerizable solution to provide varying amounts of crosslinker based on total monomer weight.

5% solids solution: A polymerizable solution was prepared by diluting about 1.2 g of Monomer Stock Solution with 1:1 v/v mixture of ethanol and deionized water to achieve about 5.0 g and adding 250 μL of S-BP. Various amounts of MBA was added to the polymerizable solution to provide varying amounts of crosslinker based on total monomer weight.

For each example, a 9 cm×12 cm piece of polyamide membrane (single reinforced layer NYLON 6.6, three zone membrane, nominal pore size 1.3-1.6 μm, product number BK080 (previously available from 3M Purification, Inc., Meridan Conn.)) was placed on a piece of polyester (PET) film and approximately 4.5 mL of polymerizable solution was pipetted onto the top surface of the membrane. The solution was allowed to soak into the membrane for about 1 minute. A second polyester film was placed on top of the substrate to form a "sandwich" construction of PET/coated polyamide/PET. A 2.28 kg weight was rolled over the top of the sandwich construction and the excess coating solution that was squeezed out was removed. The construction was then irradiated using a UV stand (Classic Manufacturing, Inc., Oakdale, Minn.) equipped with 18 bulbs (Sylvania RG2 40W F40/350BL/ECO, 10 above and 8 below the substrate, 46 inches long, spaced 2 inches on center) with an irradiation time of 10 min. The polyester films were removed, and the grafted polyamide substrate was placed in a 250 mL polyethylene bottle. The bottle was filled with 0.9 wt % saline, sealed, and shaken for 30 minutes to wash off residual monomer or ungrafted polymer. The saline was poured off, replaced with fresh saline solution, and washed for 30 min. The grafted substrate was finally washed for 30 min with deionized water and allowed to dry. The resulting substrates were tested for deionized water absorption following the Test method for liquid absorption amount described above. The results are shown in Table 1.

TABLE 1

| % MBA | Monomer 5% Solids | Monomer 10% Solids Water $A_x$ (g/g) | Monomer 15% Solids | Monomer 20% Solids |
|---|---|---|---|---|
| 1.0 | 4.1 | 2.5 | 2.4 | 2.8 |
| 0.5 | 2.0 | 3.3 | 11.6 | 12.4 |
| 0.25 | NT | 3.8 | 3.0 | 13.3 |

NT = not tested

Comparative Example C2

The procedure from Comparative Example C1 was similarly followed except that the polyamide was replaced with a polypropylene spun-bond melt blown spun-bond (SMS) nonwoven web (50 gsm, available under the trade designation "4148 KIARA FILTRATION MEDIA", a 20% 4-point square bond; available from PGI Polymers Inc., Mooresville, N.C.). The polymerizable solution as described in Comparative Example C1comprising 0.5% MBA was used. Deionized water and 0.9% wt/wt saline solution absorption amounts were measured following the Test method for liquid absorption amount described above and the results are shown in Table 2.

TABLE 2

| Test Liquid | Monomer 10% Solids $A_x$ (g/g) | Monomer 15% Solids $A_x$ (g/g) | Monomer 20% Solids $A_x$ (g/g) |
|---|---|---|---|
| Water | 3.0 | 11.0 | 53.2 |
| Saline | 2.8 | 5.2 | 16.0 |

Comparative Example C3

The procedure from Comparative Example C1 was similarly followed except that the polyamide was replaced two different polypropylene nonwovens:

(1) White PP: a white spunbond material of 12-15 gsm and (2) Blue PP: a blue thermobonded material of 18 gsm basis weight (available from Shalag Industries, Ltd., Oxford, N.C., product number SH-PPL-18B).

The polypropylene sheet was used individually or layered (2 sheets or 3 sheets). The polymerizable solution as described in Comparative Example C1 comprising 20% solids and 0.5% MBA was used. Deionized water and 0.9% wt/wt saline solution absorption was measured following the Test method for liquid absorption amount and Test method for liquid absorption rate described above. The results for liquid absorption amount are shown in Table 3. The liquid absorption rate for the various samples showed absorption times of about 90 to >120 sec, possibly due to the "gel-block" phenomenon.

TABLE 3

| Number of | White PP | | Blue PP | |
|---|---|---|---|---|
| layers | water $A_x$ (g/g) | Saline $A_x$ (g/g) | water $A_x$ (g/g) | Saline $A_x$ (g/g) |
| 1 | 97.4 | 19.4 | 111.5 | 23.0 |
| 2 | 68.2 | 14.3 | 70.1 | 16.4 |
| 3 | 50.0 | 13.6 | 44.6 | 15.4 |

Example 1

A polymerizable solution was prepared by adding 2-hydroxyethylmethacrylate (HEMA, 20% by weight based on the weight of acrylic acid) to a neutralized acrylic acid solution prepared as in Comparative Example C1 and diluting with a 1:1 v/v mixture of ethanol/deionized water to maintain an overall 20% wt/wt total monomer solution. Polymerizable solutions (5 g each) were prepared as described in Comparative Example C1 by adding S-BP and varying the amounts of MBA to provide varying amounts of crosslinker based on total monomer weight. These polymerizable solutions were coated and grafted onto the Blue PP (2 layers). The coating process was modified slightly from that described in Comparative Example C1 in that the 2.28 kg weight was not used to remove excess polymerizable solution. Instead, the top PET film, which was adhesively connected to the bottom PET film was gently laid on top of the coated substrate and the weight of the top PET was substantial enough to squeeze out excess polymerizable solution. The grafted materials were then washed, dried, and evaluated for water and saline absorption (both absorption rate and amount). Washing was accomplished by soaking the grafted composites in the appropriate wash liquid (0.9% saline or deionized water, 500 mL of liquid per substrate piece) for 30 min with occasional gentle agitation. The same sequence of three washes as before was used. Results are shown in Table 4. The results show that absorption rate can be increased by the combination of the second monomer and an increase in crosslink density. This is accomplished with little or no loss in the amount of fluid absorbed.

TABLE 4

| [MBA] | Water | | 0.9% Saline | |
|---|---|---|---|---|
| (%) | $A_t$ (sec) | $A_x$ (g/g) | $A_t$ (sec) | $A_x$ (g/g) |
| 1 | 93 | 60.9 | >120 | 17.5 |
| 2 | 23 | 52.7 | >120 | 22.6 |
| 3 | 12 | 54.4 | 15 | 18.5 |
| 4 | 6 | 46.3 | 9 | 21.9 |
| 5 | 5 | 36.3 | 8 | 18.6 |
| 7.5 | 41 | 32.4 | 104 | 7.6 |
| 10 | >120 | 13.2 | >120 | 6.6 |

Example 2

Polymerizable solutions with various amounts of MBA were prepared as described in Example 1 except that N,N-dimethylacrylamide (DMA) was used in place of HEMA. The samples were coated, grafted, washed, and dried as in Example 1 above and tested for absorption with deionized water following the Test method for liquid absorption amount. The results are shown in Table 5.

TABLE 5

| [MBA] | Water | |
|---|---|---|
| (%) | $A_t$ (sec) | $A_x$ (g/g) |
| 0.5 | 89 | 16.6 |
| 1 | 3 | 6.4 |
| 1.5 | 7 | 9.8 |
| 2 | >120 | 20.2 |
| 3 | >120 | 20.3 |

Examples 3-7

Polymerizable solutions were prepared utilizing various second monomers and varying amounts of polyethyleneglycoldiacrylate (PEGDA, MW 575, Sigma-Aldrich, Milwaukee, Wis.) as crosslinker. Solutions were prepared by mixing the Monomer Stock Solution with the ingredients listed below. Examples 3, 4, 5, and 7 all contain 20% of the second monomer by weight based on total acrylic acid weight. Examples 4-7 each contain the crosslinker molar equivalent of 0.5% MBA, while Example 3 contains the crosslinker molar equivalent of 3% MBA.

Example 3—Acrylic acid solution (4 mL), HEMA (0.1852 mL), PEGDA (0.1004 mL), 1:1 v/v ethanol/DI water (0.815 mL).

Example 4—Acrylic acid solution (4 mL), Acrylamide (0.2 grams), PEGDA (0.01665 mL), 1:1 v/v ethanol/DI water (1.0 mL).

Example 5—Acrylic acid solution (4 mL), Acrylamide (0.2 grams), MBA (0.05 mL of a 0.1 g/mL solution in DI water), 1:1 v/v ethanol/DI water (1.0 mL).

Example 6—Acrylic acid solution (5 mL), PEGDA (0.01665 mL)

Example 7—Acrylic acid solution (4 mL), Acrylamide (0.1 gram), HEMA (0.0926 mL), MBA (0.05 mL of a 0.1 g/mL solution in DI water).

Each polymerizable solution was formulated with S-BP as described in Comparative Example C1, and coated, grafted, washed, and dried as described in Example 1. The samples were tested for absorption with deionized water and saline following the Test method for liquid absorption amount described above. The results are shown in Table 6.

TABLE 6

| | Water | | 0.9% Saline | |
|---|---|---|---|---|
| Example | $A_t$ (sec) | $A_x$ (g/g) | $A_t$ (sec) | $A_x$ (g/g) |
| 3 | >120 | 43.2 | >120 | 5.4 |
| 4 | >120 | 49.9 | >120 | 16.5 |
| 5 | >120 | 49.4 | >120 | 14.7 |
| 6 | >120 | 40.1 | >120 | 16.6 |
| 7 | >120 | 51.9 | >120 | 11.9 |

Example 8

Polymerizable solutions were prepared as described before with the Monomer Stock Solution, S-BP along with 2-acrylamido-2-methyl-1-propanesulfonic acid, sodium salt (AMPS-Na, 50% wt/wt in water, Lubrizol, Wickliffe, Ohio) to and 0.5% MBA by weight based on acrylic acid. AMPS-Na was added at the 5, 7.5, and 10% by weight levels based on the acrylic acid amount. Blue PP (2 layers) were coated, grafted, washed, and dried as described in Example 1 and tested for absorption with deionized water and saline following the Test method for liquid absorption amount described above. The results are shown in Table 7.

TABLE 7

| AMPS-Na | Water | | 0.9% Saline | |
|---|---|---|---|---|
| (%) | $A_t$ (sec) | $A_x$ (g/g) | $A_t$ (sec) | $A_x$ (g/g) |
| 5 | >120 | 15.4 | >120 | 8.8 |
| 7.5 | >120 | 16.6 | 113 | 7.7 |
| 10 | 82 | 23.6 | 110 | 7.3 |

Example 9

Methylenebisacrylamide (MBA, 0.48 grams) was added to the Monomer Stock Solution to provide 4% crosslinker by weight relative to the acrylic acid to provide a first solution.

A second solution (20% wt/wt) was prepared by dissolving 2-hydroxyethylmethacrylate (HEMA, 12 grams) in 1:1 v/v ethanol/deionized water and diluting to a total of 60 grams. MBA (0.48 grams) was added to provide 4% crosslinker by weight based on HEMA.

Polymerizable solutions were prepared (5 grams each) by mixing various ratios of the first and the second solutions so as to provide between 5% and 40% co-monomer HEMA by weight based on total monomer. Each polymerizable solution was formulated with 250 µL of S-BP, coated and grafted onto the blue PP nonwoven (2 layers), washed, and dried as described in Example 1. Saline and deionized water absorption was measured following the Test method for liquid absorption amount described above, except that absorption by the entire coated composite was measured rather that the 24 mm diameter disks, a sufficient volume of liquid was used for the test method, and only one replicate was done. Results are listed in Table 8.

TABLE 8

| HEMA | Water | | 0.9% Saline |
|---|---|---|---|
| (%) | $A_t$ (sec) | $A_x$ (g/g) | $A_x$ (g/g) |
| 5 | 8 | 71.1 | 19.1 |
| 10 | 31 | 91.7 | 26.1 |
| 15 | 20 | 96.3 | 28.3 |
| 20 | 16 | 82.9 | 31.2 |
| 25 | 8 | 21.3 | 8.6 |
| 30 | >120 | 7.9 | 5.9 |
| 40 | >120 | 6.4 | 5.5 |

Example 10

Polymerizable solutions were prepared containing various ratios of acrylamide and acrylic acid (75% neutralized) by a procedure similar to that described in Example 1. Amounts of acrylamide used were 2%, 5%, 10%, and 20% by weight based on total monomer weight. Polymerizable solutions were formulated containing 2% MBA by weight based on total monomer content and S-BP was added as described in Comparative Example C1. Blue PP (2 layers) were coated, grafted, washed, dried and evaluated as described in Example 1. All four samples (2%, 5%, 10% and 20% of acrylamide) absorbed between 20-30 grams deionized water per gram of grafted composite, but all displayed an absorption time of >120 sec.

Example 11

A polymerizable solution was prepared similar to Example 1 using S-BP and comprising 20% by weight HEMA and 80% by weight acrylic acid (75% neutralized) with either 5% or 10% MBA (based on the total monomer weight) and various amounts of polyethyleneglycol 6000 (PEG 6000). Blue PP (2 layers) were coated, grafted, washed, dried and evaluated as described in Example 1. The results are shown in Table 9 using 5% MBA and Table 10 using 10% MBA.

TABLE 9

| | Water | | 0.9% Saline | |
|---|---|---|---|---|
| PEG (%) | $A_t$ (sec) | $A_x$ (g/g) | $A_t$ (sec) | $A_x$ (g/g) |
| 5 | 50 | 19.5 | 107 | 9.8 |
| 10 | 75 | 13.2 | 110 | 7.8 |
| 15 | 78 | 14.5 | 100 | 8.1 |
| 20 | 73 | 15.7 | >120 | 7.9 |

TABLE 10

| | Water | | 0.9% Saline | |
|---|---|---|---|---|
| PEG (%) | $A_t$ (sec) | $A_x$ (g/g) | $A_t$ (sec) | $A_x$ (g/g) |
| 5 | 26 | 8.1 | 29 | 6.2 |
| 10 | 20 | 7.9 | 18 | 6.3 |
| 15 | 19 | 9.3 | 30 | 5.9 |
| 20 | 30 | 7.9 | 28 | 6.6 |

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. An absorbent article comprising:
   a first substrate; and
   a layer of copolymer irreversibly bonded onto the first substrate to form a core, wherein the core comprises acidic functional groups,
   wherein the copolymer is derived from:
      a first monomer selected from a (meth)acrylic acid or salt thereof;
      a second monomer, wherein the second monomer is hydrophilic; and
      greater than 1 wt % of a third monomer based on the total weight of monomers used, wherein the third monomer is a hydrophilic crosslinking monomer,
   wherein at least 50% of the acidic functional groups in the core are neutralized with salt forming cations.

2. The absorbent article of claim 1, wherein the second monomer is selected from at least one of 2-hydroxyethylmethacrylate, 2-hydroxypropyl(meth)acrylate, 3-hydroxypropyl(meth)acrylate, N,N-dimethylacrylamide, and acrylamide.

3. The absorbent article of claim 1, wherein the copolymer comprises at least 1% of the second monomer.

4. The absorbent article of claim 1, wherein the third monomer is selected from at least one of methylenebisacrylamide and polyethyleneglycoldiacrylate.

5. The absorbent article of claim 1, further comprising a second layer, wherein the second layer is a liquid pervious layer.

6. The absorbent article of claim 5 further comprising a third layer, wherein the third layer is a liquid impervious layer and the core sandwiched between the second layer and the third layer.

7. The absorbent article of claim 5, wherein the second layer is selected from polyester, polyolefin, rayon, cotton, and combinations thereof.

8. The absorbent article of claim 1, wherein the first substrate is selected from at least one of a thermoplastic and a fabric.

9. The absorbent article of claim 1, wherein the absorbent article is selected from a diaper, a feminine hygiene pad, an animal hygiene pad, a wound care article, and a chemical absorbent pad.

10. The absorbent article of claim 1, wherein the first substrate is selected from at least one of a polypropylene, polyethylene, Nylon X, cotton, and cellulose.

11. The absorbent article of claim 1, wherein the copolymer comprises no more than 30% by weight of a second monomer versus the total weight of monomer.

12. The absorbent article of claim 1, wherein the copolymer comprises at least 3 and no more than 10% by weight of the third monomer.

13. The absorbent article of claim 1, wherein the copolymer comprises at least 5% and no more than 20% by weight of the second monomer versus the total weight of monomer.

14. The absorbent article of claim 1, wherein the copolymer comprises 40 to 97% by weight of the first monomer versus the total weight of monomer.

15. The absorbent article of claim 1, wherein the copolymer comprises a fourth monomer, wherein the fourth monomer is not hydrophilic.

16. The absorbent article of claim 1, wherein the second monomer comprises a hydroxyl group-, containing monomer.

17. A method of making an absorbent article comprising:
  (a) contacting a polymerizable solution to a first substrate, wherein the polymerizable solution comprises (i) a first monomer selected from a (meth)acrylic acid or salt thereof; (ii) a second monomer, wherein the second monomer is hydrophilic; and (iii) greater than 1 wt % of a third monomer based on the total weight of monomers used, wherein the third monomer is a hydrophilic crosslinking monomer; and
  (b) polymerizing the polymerizable solution to irreversibly bond a copolymer onto the first substrate forming a core, wherein the core comprises acidic functional groups, and
  wherein at least 50% of the acidic functional groups in the core are neutralized with salt forming cations.

18. The method of claim 17, wherein the polymerizable solution further comprises a Type II photoinitiator.

19. The method of claim 17, further comprising washing the core.

20. The method of claim 17, where the absorbent article is a roll good.

* * * * *

UNITED STATES PATENT AND TRADEMARK OFFICE
CERTIFICATE OF CORRECTION

PATENT NO.        : 11,076,999 B2
APPLICATION NO.   : 15/304139
DATED             : August 3, 2021
INVENTOR(S)       : Rasmussen et al.

Page 1 of 1

It is certified that error appears in the above-identified patent and that said Letters Patent is hereby corrected as shown below:

In the Claims

<u>Column 22</u>
Line 5, In Claim 16, delete "," after "group-".

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*